US012053632B2

(12) United States Patent
Block et al.

(10) Patent No.: US 12,053,632 B2
(45) Date of Patent: Aug. 6, 2024

(54) METHODS AND SYSTEMS FOR MAKING ELECTRICAL STIMULATION ADJUSTMENTS BASED ON PATIENT-SPECIFIC FACTORS

(71) Applicant: Boston Scientific Neuromodulation Corporation, Valencia, CA (US)

(72) Inventors: Jessica Block, Sherman Oaks, CA (US); Andrew James Haddock, Los Angeles, CA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1007 days.

(21) Appl. No.: 16/938,745

(22) Filed: Jul. 24, 2020

(65) Prior Publication Data

US 2021/0023374 A1    Jan. 28, 2021

Related U.S. Application Data

(60) Provisional application No. 62/879,256, filed on Jul. 26, 2019.

(51) Int. Cl.
*A61N 1/36* (2006.01)
*A61B 5/24* (2021.01)
(Continued)

(52) U.S. Cl.
CPC ............ *A61N 1/36062* (2017.08); *A61B 5/24* (2021.01); *A61B 5/316* (2021.01); *A61N 1/0551* (2013.01);
(Continued)

(58) Field of Classification Search
CPC .............. A61N 1/36062; A61N 1/0551; A61N 1/36132; A61N 1/36139; A61N 1/36135; A61B 5/24; A61B 5/316
See application file for complete search history.

(56) References Cited

U.S. PATENT DOCUMENTS 4,625,730 A    12/1986   Fountain et al.
5,697,958 A    12/1997   Paul et al.
(Continued)

FOREIGN PATENT DOCUMENTS

EP          2926728       10/2015
WO       2006/119131      11/2006
(Continued)

OTHER PUBLICATIONS

Morrison, G., Lorig, R., Brodkey, J. S., & Nulsen, F. E. (1975). Electrospinogram and spinal and cortical evoked potentials in experimental spinal cord trauma. Journal of Neurosurgery, 43(6), 737-741 (Year: 1975).*
(Continued)

*Primary Examiner* — Paula J Stice
(74) *Attorney, Agent, or Firm* — Branch Partners PLLC; Bruce E. Black (57) ABSTRACT

Methods and systems for making adjustments to electrical stimulation based on patient-specific factors can includes the following instructions or actions: receiving information regarding at least one of i) electrical response of patient tissue, ii) patient response to stimulation, or iii) an arrangement of the implanted lead or the electrodes of the implanted lead with respect to patient anatomy; and calculating an electrode weight for each of a plurality of the electrodes of the implanted lead based on the received information.

20 Claims, 8 Drawing Sheets

(51) Int. Cl.
  *A61B 5/316* (2021.01)
  *A61N 1/05* (2006.01)
(52) U.S. Cl.
  CPC ..... *A61N 1/36132* (2013.01); *A61N 1/36139* (2013.01)

(56) References Cited

U.S. PATENT DOCUMENTS

| | | | |
|---|---|---|---|
| 5,702,429 A | 12/1997 | King | |
| 5,902,236 A | 5/1999 | Iverson | |
| 5,902,249 A | 5/1999 | Lyster | |
| 5,913,882 A | 6/1999 | King | |
| 6,061,593 A | 5/2000 | Fischell et al. | |
| 6,181,969 B1 | 1/2001 | Gord | |
| 6,516,227 B1 | 2/2003 | Meadows et al. | |
| 6,560,490 B2 | 5/2003 | Grill et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,895,280 B2 | 5/2005 | Meadows et al. | |
| 7,024,247 B2 | 4/2006 | Gliner et al. | |
| 7,136,695 B2 | 11/2006 | Pless et al. | |
| 7,244,150 B1 | 7/2007 | Brase et al. | |
| 7,424,322 B2 | 9/2008 | Lombardi et al. | |
| 7,437,193 B2 | 10/2008 | Parramon et al. | |
| 7,450,992 B1 | 11/2008 | Cameron | |
| 7,450,997 B1 | 11/2008 | Pianca et al. | |
| 7,603,179 B1 | 10/2009 | Grandhe | |
| 7,672,734 B2 | 3/2010 | Anderson et al. | |
| 7,761,165 B1 | 7/2010 | He et al. | |
| 7,783,359 B2 | 8/2010 | Meadows | |
| 7,792,590 B1 | 9/2010 | Pianca et al. | |
| 7,809,446 B2 | 10/2010 | Meadows | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,255,057 B2 | 8/2012 | Fang et al. | |
| 8,271,094 B1 | 9/2012 | Moffitt et al. | |
| 8,295,944 B2 | 10/2012 | Howard et al. | |
| 8,335,664 B2 | 12/2012 | Eberle | |
| 8,352,030 B2 | 1/2013 | Denison | |
| 8,364,278 B2 | 1/2013 | Pianca et al. | |
| 8,391,985 B2 | 3/2013 | McDonald | |
| 8,606,362 B2 | 12/2013 | He et al. | |
| 8,620,436 B2 | 12/2013 | Parramon et al. | |
| 8,688,235 B1 | 4/2014 | Pianca et al. | |
| 8,768,453 B2 | 7/2014 | Parramon et al. | |
| 9,044,155 B2 | 6/2015 | Strahl | |
| 9,061,140 B2 | 6/2015 | Shi et al. | |
| 9,113,801 B2 | 8/2015 | DiLorenzo | |
| 9,119,964 B2 | 9/2015 | Marnfeldt | |
| 9,155,892 B2 | 10/2015 | Parker et al. | |
| 9,248,274 B2 | 2/2016 | Troosters et al. | |
| 9,248,279 B2 | 2/2016 | Chen et al. | |
| 9,265,431 B2 | 2/2016 | Hincapie Ordonez et al. | |
| 9,302,112 B2 | 4/2016 | Bomzin et al. | |
| 9,381,356 B2 | 7/2016 | Parker et al. | |
| 9,386,934 B2 | 7/2016 | Parker et al. | |
| 9,399,132 B2 | 7/2016 | Parramon et al. | |
| 9,403,013 B2 | 8/2016 | Walker et al. | |
| 9,409,020 B2 | 8/2016 | Parker | |
| 9,526,897 B2 | 12/2016 | Chen et al. | |
| 9,533,148 B2 | 1/2017 | Carcieri | |
| 9,731,116 B2 | 8/2017 | Chen | |
| 9,872,990 B2 | 1/2018 | Parker et al. | |
| 9,974,455 B2 | 5/2018 | Parker et al. | |
| 10,076,667 B2 | 9/2018 | Kaula et al. | |
| 2002/0156513 A1 | 10/2002 | Borkan | |
| 2003/0139781 A1 | 7/2003 | Bradley et al. | |
| 2005/0113705 A1 | 5/2005 | Fischell et al. | |
| 2005/0246004 A1 | 11/2005 | Cameron et al. | |
| 2006/0195159 A1* | 8/2006 | Bradley | A61N 1/36185 607/48 |
| 2007/0150036 A1 | 6/2007 | Anderson | |
| 2008/0146894 A1 | 6/2008 | Bulkes et al. | |
| 2009/0105785 A1 | 4/2009 | Wei et al. | |
| 2009/0187222 A1 | 7/2009 | Barker | |
| 2009/0216141 A1 | 8/2009 | Fischell et al. | |
| 2009/0276021 A1 | 11/2009 | Meadows et al. | |
| 2010/0076535 A1 | 3/2010 | Pianca et al. | |
| 2010/0114224 A1 | 5/2010 | Krause et al. | |
| 2010/0268298 A1 | 10/2010 | Moffitt et al. | |
| 2010/0305642 A1 | 12/2010 | Dong et al. | |
| 2010/0331916 A1 | 12/2010 | Parramon et al. | |
| 2011/0004267 A1 | 1/2011 | Meadows | |
| 2011/0005069 A1 | 1/2011 | Pianca | |
| 2011/0078900 A1 | 4/2011 | Pianca et al. | |
| 2011/0130817 A1 | 6/2011 | Chen | |
| 2011/0130818 A1 | 6/2011 | Chen | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2012/0165911 A1 | 6/2012 | Pianca | |
| 2012/0188096 A1 | 7/2012 | Corndorf et al. | |
| 2012/0197375 A1 | 8/2012 | Pianca et al. | |
| 2012/0203316 A1 | 8/2012 | Moffitt et al. | |
| 2012/0203320 A1 | 8/2012 | DiGiore et al. | |
| 2012/0203321 A1 | 8/2012 | Moffitt et al. | |
| 2012/0316615 A1 | 12/2012 | DiGiore et al. | |
| 2013/0105071 A1 | 5/2013 | DiGiore et al. | |
| 2013/0197602 A1 | 8/2013 | Pianca et al. | |
| 2013/0289665 A1 | 10/2013 | Marnfeldt et al. | |
| 2014/0012341 A1 | 1/2014 | Von Arx et al. | |
| 2014/0031901 A1 | 1/2014 | Zhu et al. | |
| 2014/0194772 A1 | 7/2014 | Single et al. | |
| 2014/0236042 A1 | 8/2014 | Parker et al. | |
| 2014/0243926 A1 | 8/2014 | Carcieri | |
| 2014/0276707 A1 | 9/2014 | Jaax | |
| 2014/0277282 A1 | 9/2014 | Jaax | |
| 2014/0296737 A1 | 10/2014 | Parker et al. | |
| 2015/0018699 A1 | 1/2015 | Zeng et al. | |
| 2015/0119751 A1 | 4/2015 | Stanslaski et al. | |
| 2015/0157861 A1 | 6/2015 | Aghassian | |
| 2015/0282725 A1 | 10/2015 | Single | |
| 2015/0313487 A1 | 11/2015 | Single et al. | |
| 2015/0360038 A1 | 12/2015 | Zottola et al. | |
| 2016/0166164 A1 | 6/2016 | Obradovic et al. | |
| 2016/0287126 A1 | 10/2016 | Parker et al. | |
| 2016/0287182 A1 | 10/2016 | Single | |
| 2017/0049345 A1 | 2/2017 | Single | |
| 2017/0071490 A1 | 3/2017 | Parker et al. | |
| 2017/0113046 A1 | 4/2017 | Fried et al. | |
| 2017/0135624 A1 | 5/2017 | Parker | |
| 2017/0136243 A1 | 5/2017 | Lee et al. | |
| 2017/0157410 A1 | 6/2017 | Moffitt et al. | |
| 2017/0173335 A1 | 6/2017 | Min et al. | |
| 2017/0216587 A1 | 8/2017 | Parker | |
| 2017/0259065 A1 | 9/2017 | Baru et al. | |
| 2017/0281958 A1 | 10/2017 | Serrano Carmona et al. | |
| 2017/0296823 A1 | 10/2017 | Hershey et al. | |
| 2017/0361101 A1 | 12/2017 | Single | |
| 2018/0028083 A1 | 2/2018 | Greenhut et al. | |
| 2018/0071513 A1 | 3/2018 | Weiss et al. | |
| 2018/0071520 A1 | 3/2018 | Weerakoon et al. | |
| 2018/0071527 A1 | 3/2018 | Feldman et al. | |
| 2018/0071530 A1 | 3/2018 | Giftakis et al. | |
| 2018/0078769 A1 | 3/2018 | Dinsmoor et al. | |
| 2018/0110987 A1 | 4/2018 | Parker | |
| 2018/0117335 A1 | 5/2018 | Parker et al. | |
| 2018/0132747 A1 | 5/2018 | Parker et al. | |
| 2018/0132760 A1 | 5/2018 | Parker | |
| 2018/0133459 A1 | 5/2018 | Parker et al. | |
| 2018/0140831 A1 | 5/2018 | Feldman et al. | |
| 2018/0228391 A1 | 8/2018 | Parker et al. | |
| 2018/0228547 A1 | 8/2018 | Parker et al. | |
| 2018/0256052 A1 | 9/2018 | Parker et al. | |
| 2018/0289967 A1 | 10/2018 | Bokil | |
| 2019/0099602 A1 | 4/2019 | Esteller et al. | |

(56) References Cited

U.S. PATENT DOCUMENTS

| | | |
|---|---|---|
| 2019/0175915 A1 | 6/2019 | Brill et al. |
| 2019/0209844 A1 | 7/2019 | Esteller et al. |
| 2019/0275331 A1 | 9/2019 | Zhu |
| 2019/0290900 A1 | 9/2019 | Esteller et al. |
| 2019/0298992 A1 | 10/2019 | Zhang et al. |
| 2019/0299006 A1 | 10/2019 | Marnfeldt |
| 2019/0366094 A1 | 12/2019 | Esteller et al. |
| 2020/0155019 A1 | 5/2020 | Esteller et al. |
| 2020/0305745 A1 | 10/2020 | Wagenbach et al. |
| 2020/0376263 A1 | 12/2020 | Zhu |
| 2020/0398057 A1 | 12/2020 | Esteller et al. |
| 2021/0316139 A1 | 10/2021 | Shelton et al. |
| 2022/0148591 A1 | 5/2022 | Chao et al. |
| 2023/0181906 A1 | 6/2023 | Moore et al. |

FOREIGN PATENT DOCUMENTS

| | | |
|---|---|---|
| WO | 2012/155186 | 11/2012 |
| WO | 2015/077362 | 5/2015 |
| WO | 2017/100866 | 6/2017 |
| WO | 2017/173493 | 10/2017 |
| WO | 2017/210352 | 12/2017 |
| WO | 2017/219096 | 12/2017 |
| WO | 2021/021659 | 2/2021 |

OTHER PUBLICATIONS

International Search Report and Written Opinion for PCT Application No. PCT/US2020/043579 mailed Nov. 3, 2020.

* cited by examiner

METHODS AND SYSTEMS FOR MAKING ELECTRICAL STIMULATION ADJUSTMENTS BASED ON PATIENT-SPECIFIC FACTORS

CROSS-REFERENCE TO RELATED APPLICATIONS

This application claims the benefit under 35 U.S.C. § 119(e) of U.S. Provisional Patent Application Ser. No. 62/879,256, filed Jul. 26, 2019, which is incorporated herein by reference.

FIELD

The present invention is directed to the area of implantable electrical stimulation systems and methods of making and using the systems. The present invention is also directed to methods and systems for making adjustments to electrical stimulation based on patient-specific factors.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a system for generating stimulation parameters for delivery of stimulation through at least one of a plurality of electrodes of an implanted lead. The system includes a memory having instructions stored thereon; and a processor coupled to the memory and configured to execute the instructions, the instructions including receiving information regarding at least one of i) electrical response of patient tissue, ii) patient response to stimulation, or iii) an arrangement of the implanted lead or the electrodes of the implanted lead with respect to patient anatomy; and calculating an electrode weight for each of a plurality of the electrodes of the implanted lead based on the received information.

Another aspect is a non-transitory computer-readable medium having stored thereon instructions for execution by a processor, including receiving patient-specific information regarding at least one of i) electrical response of patient tissue, ii) patient response to stimulation, or iii) an arrangement of an implanted lead or electrodes of the implanted lead with respect to patient anatomy; and calculating an electrode weight for each of a plurality of the electrodes of the implanted lead based on the received information.

In at least some aspects, the electrical response of patient tissue includes at least one feature of an electrical response to at least one electrical pulse delivered to patient tissue by at least one of the electrodes of the implanted lead. In at least some aspects, the electrical response of patient tissue includes and electrospinogram (ESG) or at least one feature of an ESG. In at least some aspects, the electrical response of patient tissue includes at least one of an area under a curve of the ESG in a predefined time window, a range of an amplitude of the curve of the ESG in a predefined time window, a length of the curve of the ESG in a predefined time window, an energy content of the ESG in a predefined time window, a range of a derivative of the ESG in a predefined time window, a time delay of a specified signal peak of the ESG, power of the ESG in a predefined frequency band, variation of a frequency with highest energy in the ESG in a predefined frequency band, coherence changes in the ESG, a quality factor for a specified signal peak of the ESG in a predefined time window, a spectral entropy of the ESG or any other entropy-related feature of the ESG in a predefined time window; or full width at half amplitude for a specified signal peak of the ESG in a predefined time window.

In at least some aspects, the patient response to stimulation includes at least one of patient feedback (for example, patient feedback regarding a perception threshold, maximum comfort threshold, intensity of the stimulation, therapeutic description or window, sensation description, or the like or any combination thereof), clinician feedback, signals from one or more sensors, or measurements from the signals from the one or more sensors.

In at least some aspects, the arrangement of the implanted lead or electrodes with respect to the patient anatomy includes a position of the implanted lead or the electrodes within the patient anatomy. In at least some aspects, the position is determined from imaging of the implanted lead or electrodes within the patient anatomy.

In at least some aspects, the arrangement of the implanted lead or the electrodes with respect to the patient anatomy includes a lateral distance of the implanted lead or the electrodes from a center of the spinal cord, dorsal column, dorsal roots, or pedicles of the patient and a longitudinal position along the spinal cord of the patient.

In at least some aspects, the instructions further include generating stimulation parameters, using at least one of the electrode weights, for use with the implanted lead. In at least some aspects, generating stimulation parameters includes generating an adjustment, using at least one of the electrode weights, to previous stimulation parameters for use with the implanted lead. In at least some aspects, generating the adjustment includes generating the adjustment in response to a steering instruction.

In at least some aspects, the electrode weights are in a range of 0 to 1. In at least some aspects, receiving information includes individually for each of a plurality of the electrodes, delivering an electrical pulse using the electrode and receiving an electrical response to the delivery, wherein the information is generated from the received electrical responses. In at least some aspects, the information is patient-specific information.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to methods and systems for making adjustments to electrical stimulation based on patient-specific factors.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated herein by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, or peripheral nerve stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for spinal cord stimulation, but it will be understood that any of the leads can be used for applications other than spinal cord stimulation, including deep brain stimulation, peripheral nerve stimulation, dorsal root ganglion stimulation, sacral nerve stimulation, or stimulation of other nerves, muscles, and tissues.

Figure 1:
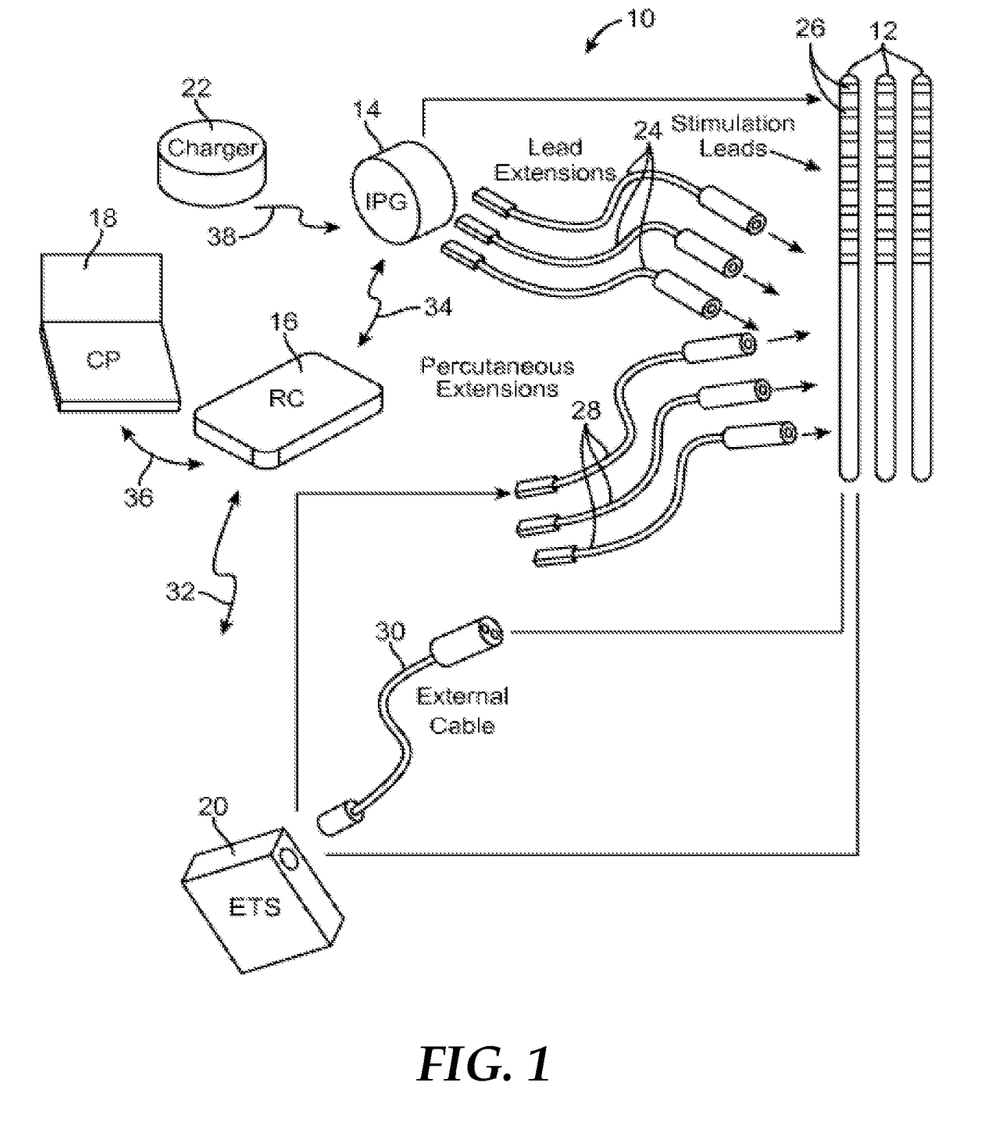
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity or at any other suitable site. The implantable pulse generator can have multiple stimulation channels which may be independently programmable to control the magnitude of the current stimulus from each channel. In some embodiments, the implantable pulse generator can have any suitable number of stimulation channels including, but not limited to, 4, 6, 8, 12, 16, 32, or more stimulation channels. The implantable pulse generator can have one, two, three, four, or more connector ports, for receiving the terminals of the leads or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated herein by reference.

Figure 2A:
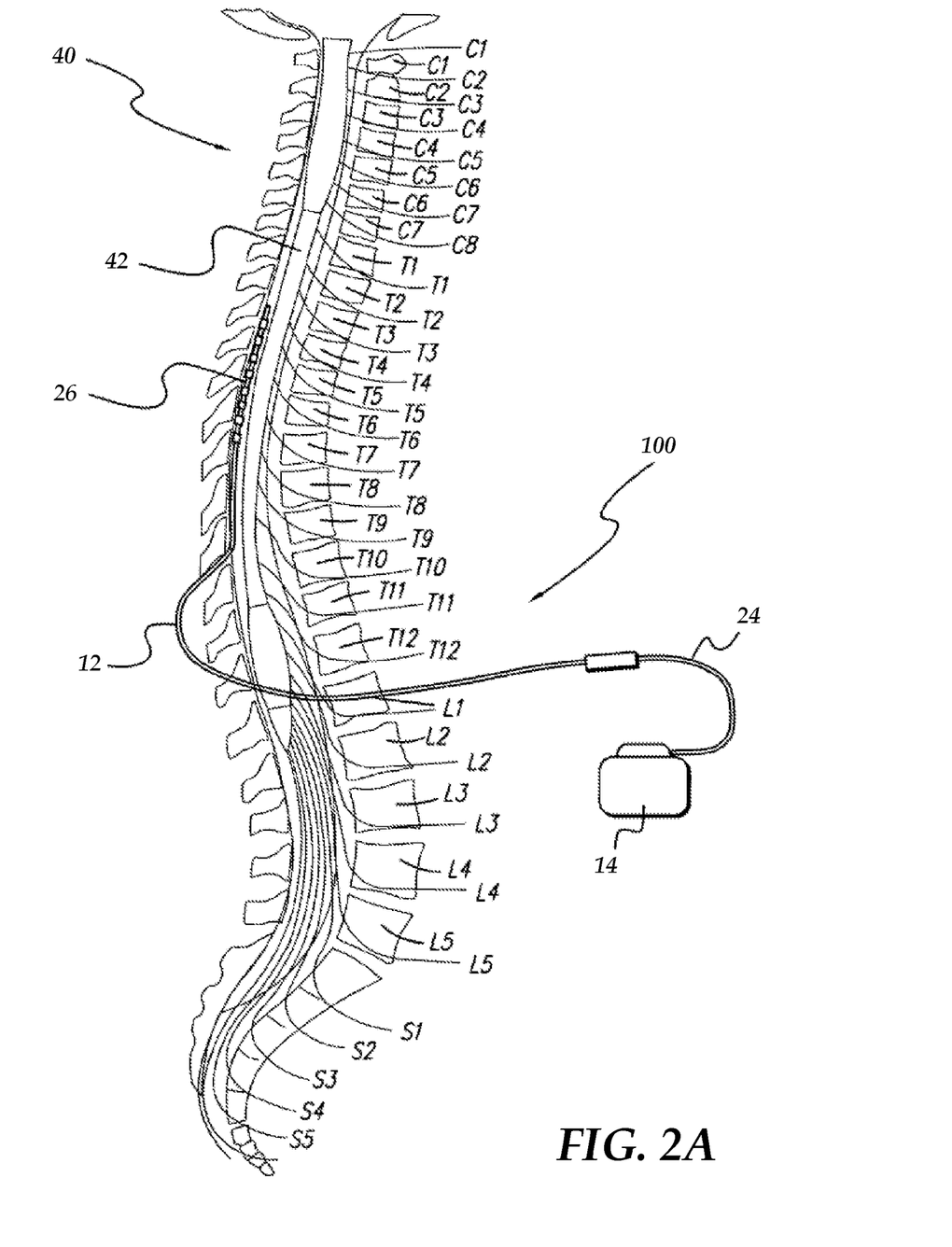
FIGS. 2A to 2E are schematic views of different arrangements with one or more leads implanted along the spinal cord.

FIG. 2A illustrates one embodiment of a spinal cord stimulation (SCS) system 100 implanted in a patient 40. The SCS system 100 includes an IPG 14 that generates electrical stimulation pulses used for stimulation. An array of electrodes 26 at or near the distal end of an implanted stimulation lead 12 is inserted into the epidural space next to the spinal cord 42. Optionally, a lead extension 24 may be used to connect the lead 12 to the IPG 14.

As illustrated in FIG. 2A, the vertebral spacing along the spinal cord 42 varies from the cervical region (C1-C8) to the thoracic region (T1-T12) to the lumbar region (L1-L5). In particular, the lower thoracic region and the lumbar region have substantial variation in spacing. Moreover, the spacing between adjacent vertebrae will be different from patient to patient due to anatomical differences as well as spinal cord development and degeneration. Particularly at these levels, the position on the electrodes on the implanted lead may be patient-variable even when the lead is implanted at the same spinal cord level. Nerve fiber activation by electrical stimulation using the electrodes of the lead can be substantially different depending on the relative location of the electrode to the nerve fiber or other neural elements to be stimulated.

Figure 2B:
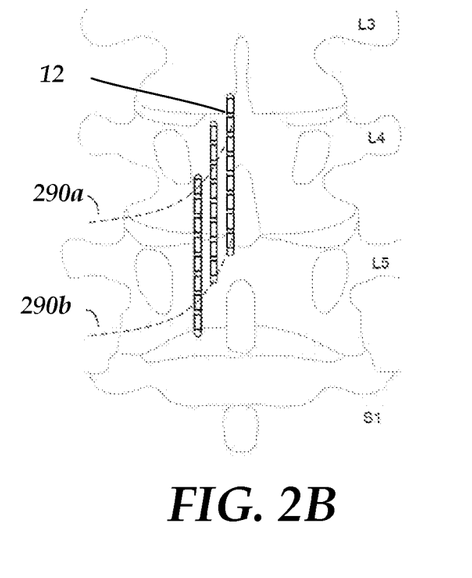
Figure 2C:
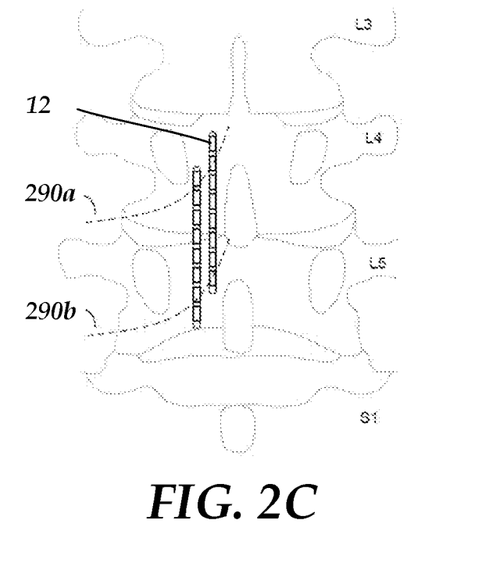
Figure 2D:
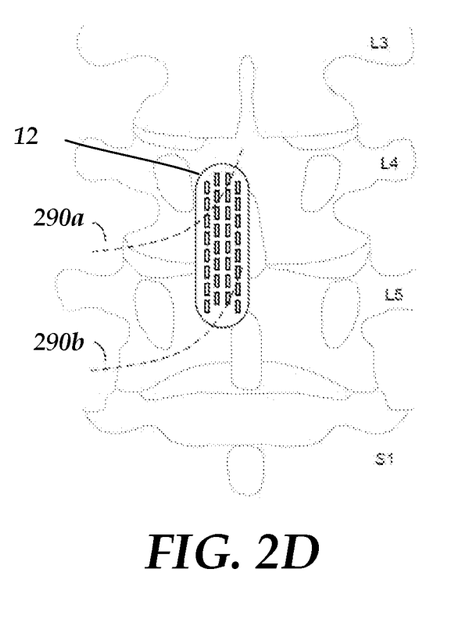
Figure 2E:
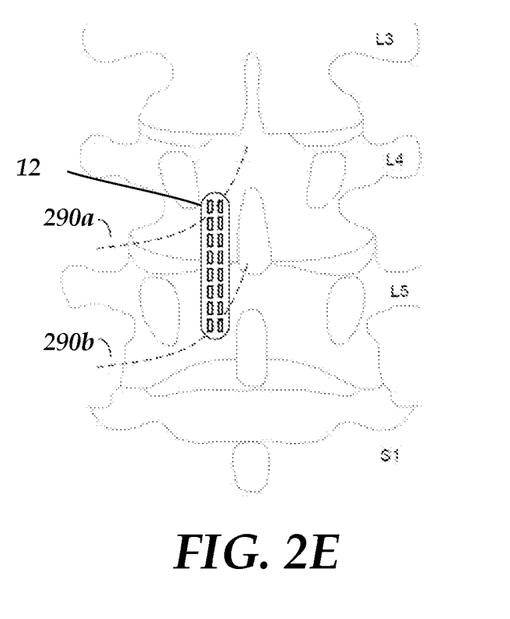

FIGS. 2B to 2E illustrate the placement of leads 12 relative to dorsal roots 290*a*, 290*b* and illustrate that the electrodes of the leads can be positioned at different distances from the dorsal roots with some electrodes overlapping or near the dorsal roots and other electrodes more distant from the dorsal roots. FIGS. 2B and 2C illustrate percutaneous leads and FIGS. 2D and 2E illustrate paddle leads. The methods, systems, and arrangements described below can be utilized with leads placed midline, lateral of midline, near the dorsal columns, near the dorsal roots, or near the pedicals, or any other suitable placement site.

In at least some electrical stimulation systems, the selection of electrodes, the electrode fractionalization (i.e., the fraction of the total current or voltage applied to each of the selected electrodes), the total amplitude, or other parameters or any combination thereof can be altered or adjusted to steer the stimulation up or down the lead (or when using segmented electrodes around the circumference of the lead.) When steering the stimulation, current systems utilize a combination of one or more of the electrode spacing, the spinal cord level(s) at which the lead is implanted, and, for SCS, the average cerebral spinal fluid thickness at the spinal cord level to determine adjustments of the amplitude to steer or reliably increase or decrease stimulation. As indicated above, however, at the level of the lumbar roots (and possibly other portions of the spinal cord), neural activation can drastically change depending on the relative location of an electrode with respect to the neural elements to be stimulated. This may also be the case when the lead is positioned laterally of the center of the spinal cord, particularly as the lateral distance from the spinal cord is increased and the dorsal roots, instead of the dorsal column, becomes the primary target for stimulation.

To better manage determination or adjustments of the amplitude or other stimulation parameters for steering the stimulation or for determining efficacious parameters, information can be obtained from one or more of a variety of sources to produce electrode weights that can be used to modify the determination or adjustments to the amplitude or other stimulation parameters. In at least some embodiments, this information is patient-specific so that the determination or adjustments are tailored to the patient. Examples of such information include, but are not limited to, electrospinogram or other electrical response measurements or features of such response measurements, anatomical information (which may be include patient-specific imaging or information), patient feedback of perception or discomfort during stimulation (for example, patient feedback regarding a perception threshold, maximum comfort threshold, intensity of the stimulation, therapeutic description or window, sensation description, or the like or any combination thereof), clinician feedback, sensor measurements, or the like or any combination thereof.

In at least some embodiments, the electrode weights can reflect the efficacy of the individual electrodes in stimulating patient tissue. (The electrode weights do not represent the fractionalization, e.g., the distribution, of the stimulation signal between the electrodes, but rather represent the effectiveness of the electrode in stimulating the target tissue.) That efficacy can vary substantially with, for example, the position of the electrode relative to the tissue to be stimulated, such as, for example, the dorsal roots of the spinal cord. As an example, due to the position of the lead and the spacing of the electrodes along the lead, when implanted some electrodes may be positioned nearer the tissue to be stimulated (for example, the dorsal roots) than other electrodes and, therefore, generally have a higher efficacy in producing stimulation. This may be evident, for example, when the spacing between the electrodes and the spacing between dorsal roots at different levels of the spinal cord differ substantially so that, when implanted, some electrodes will be positioned near the dorsal roots and some electrodes positioned further away. These latter electrodes may require application of higher amplitude stimulation to produce a similar effect to the electrodes that are nearer a dorsal root. Although the dorsal roots are used as an example, it will be understood that this applies to other physiological elements and arrangements of the spinal cord or other anatomical features and elements.

A variety of different types of information can be used to determine the electrode weights. For example, images of the implanted lead and surrounding anatomy can be used to identify the positions of the electrodes and lead, such as, for example, the how far lateral the lead is relative to the center of the spinal cord, dorsal column, dorsal roots, cauda *equina*, or neural elements to be stimulated; alignment of the lead or electrodes with the pedicles or other portions of the vertebrae; alignment of the lead or electrodes with the dorsal roots, or the like or any combination thereof. Such information may be obtained using a fluoroscope or any other suitable imaging technique or may be based on the clinician's knowledge or estimate of where the lead or electrodes were implanted.

Another source of information is the patient response to stimulation. In at least some embodiments, when stimulated the patient may provide feedback regarding the efficacy (e.g., pain relief or paresthesia) or discomfort that results from the stimulation. The patient feedback may be made verbally to a clinician or other individual that records the feedback or may be entered into a RC, CP, or other device by the patient, clinician, or other individual. In at least some embodiments, a clinician or individual other than the patient may observe the patient response and provide the feedback into a RC, CP, or other device. In at least some embodiments, the patient response can be measured or monitored using one or more sensors. Examples of suitable sensors include external sensors disposed on or near the patient's body or internal sensors which may be implanted with, or separate from, the IPG or lead, or any combination of internal or external sensors. The sensors may communicate measurements or analysis/features of the sensor measurements to the CP, RC, IPG, or other device or the measurements, analysis, or features may be received and entered by the patient, clinician, or other individual. In yet other embodiments, any combination of patient feedback, clinician feedback, or sensor measurements/analysis/features can be used to produce the information regarding patient response to stimulation.

Yet another source of information is a measurement of an electrical response to an electrical signal that can be delivered using, for example, one or more of the electrodes of the lead. In addition, the electrical response can be received by one or more of the electrodes of the lead, or other electrodes such as recording electrodes on or near the lead, and the IPG, CP, RC, or another device can analyze the received electrical response. The electrical response can be, for example, an evoked response or an evoked composite action potential (ECAP) or may even be a spontaneous response (i.e., a response that is not necessarily generated by an electrical signal from the electrodes of the lead) or any other suitable electrical response.

One example of an electrical response is an electrospinogram (ESG) that can be obtained by applying an electrical pulse to neural tissue using one or more of the electrodes of the lead. In at least some embodiments, each electrode (or a subset of the electrodes) can individually deliver the electrical pulse and an ESG corresponding to that electrode can be obtained.

Figure 3:
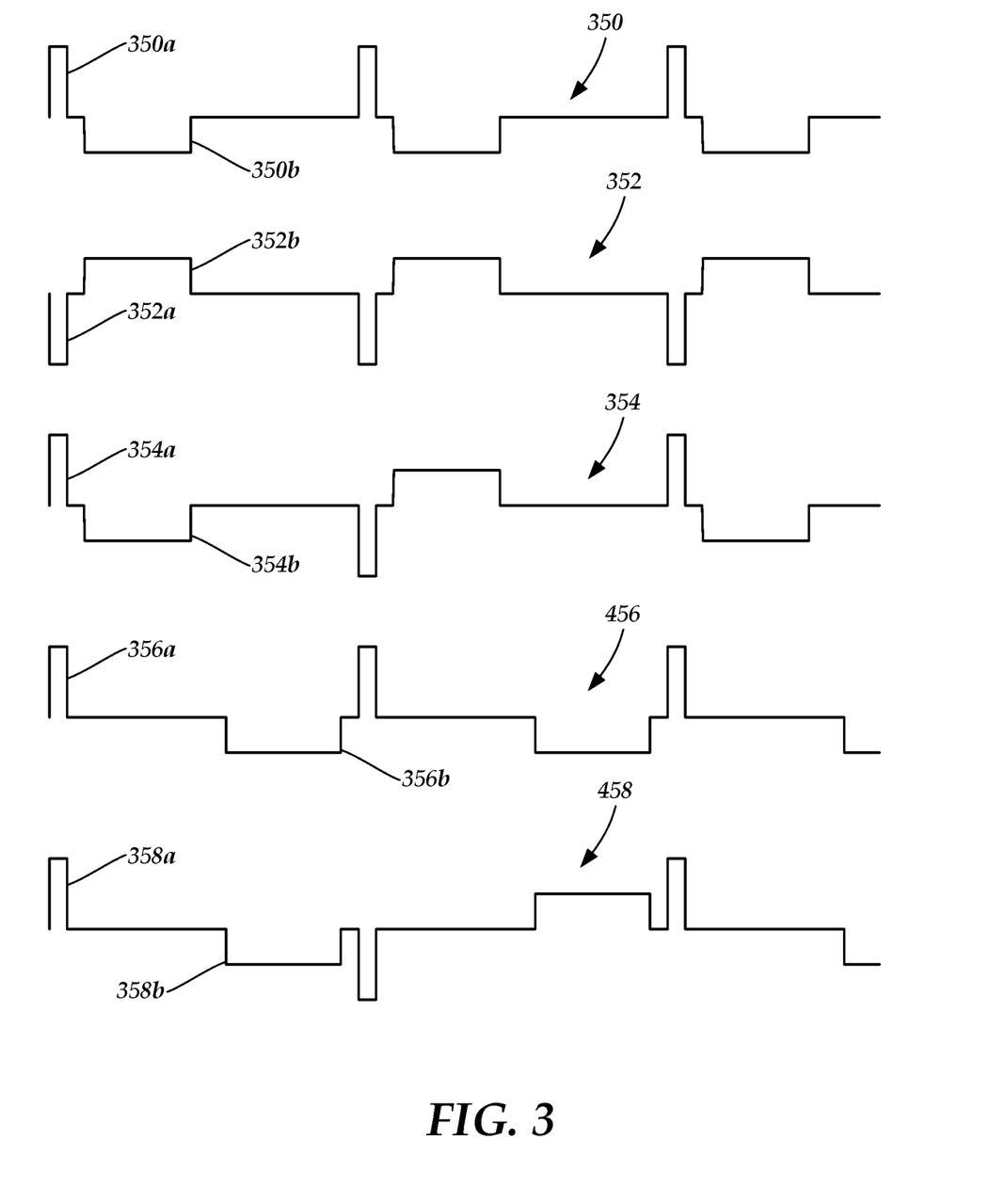
FIG. 3 illustrates five embodiments of different electrical pulse trains for producing an electrical response.

The shape of the electrical pulse, as well as its amplitude, frequency, pulse width, and the like, can be selected to enhance sensing of the ESG and may not necessarily be the same as the pulse shapes used for therapeutic stimulation. Moreover, the pulse shape can be symmetric or asymmetric and can be monophasic, biphasic, or multiphasic. FIG. 3 illustrates examples of different electrical pulses that might be used. Pulse train 350 is an example of an asymmetric, active recharge, biphasic pulse where the anodic subpulse 350a is delivered first followed by the cathodic subpulse 350b. Pulse train 352 is an example of another asymmetric, active recharge, biphasic pulse where the cathodic subpulse 352a is delivered first followed by the anodic subpulse 350b. Pulse train 354 is a third example of an asymmetric, active recharge, biphasic pulse where the first subpulse 354a alternates between anodic and cathodic and the second subpulse 354b alternates between cathodic and anodic. Pulse train 356 is a fourth example of an asymmetric, active recharge, biphasic pulse where the anodic subpulse 356a is delivered first and there is a relatively long interspace between the first subpulse 356a and the second subpulse 356b. Pulse train 358 is a fifth example of an asymmetric, active recharge, biphasic pulse that includes the relatively long interspace between the first subpulse 358a and the second subpulse 358b and the first subpulse 358a alternates between anodic and cathodic. These are examples and it will be understood that many other pulse trains can be used.

The electrodes of the lead, or other sensors/electrodes on or near the lead, can be used to receive (e.g., sense) the ESG. The ESG can be analyzed using the IPG, CP, RC, or another device to identify and measure one or more features of the ESG. The features may be evaluated in the frequency domain or time domain. Examples of features of the ESG that may be useful for produce the electrode weights include, but are not limited to, one or more of the following: area under the ESG curve in a predefined time window, the range of the ESG curve (for example, the range between a local maximum and a local minimum in a predefined time window), ESG curve length in a predefined time window, ESG energy content in a predefined time window, a range of the derivative of the ESG signal in a predefined time window, time delay of specified ESG signal peak, ESG power in a defined frequency band, variation of the ESG centroid frequency (i.e., the frequency with highest energy) in a defined frequency band, mutual information, a spectral entropy of the ESG or any other entropy-related feature of the ESG in a predefined time window, standard deviation of any of the previous metrics, coherence changes in the ESG, or a quality factor or FWHM (full width at half amplitude) for specified ESG peak in a predefined time window.

Figure 4:
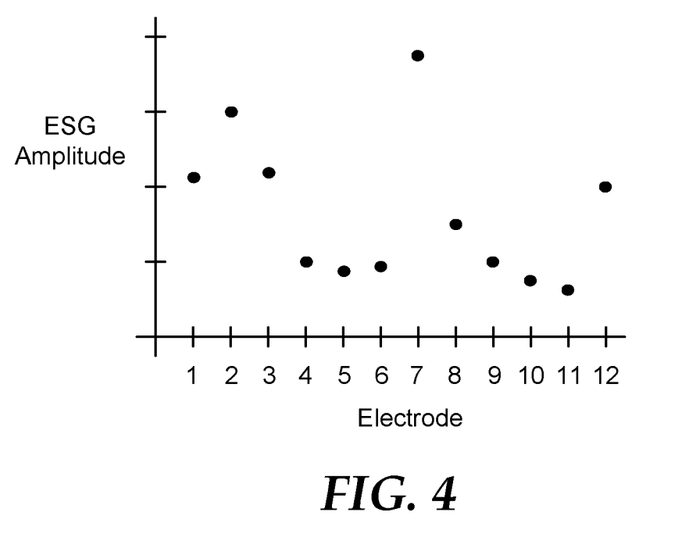
FIG. 4 is a graph of electrospinogram (ESG) amplitude for a set of electrodes.

As an example of an ESG feature that can be used for determining electrode weights, FIG. 4 is a graph of ESG amplitude as a function of the electrode that delivers the electrical pulse to initiate the ESG. In the example illustrated in FIG. 4, electrodes 2 and 7 appear to elicit a higher ESG amplitude than other electrodes.

Figure 5:
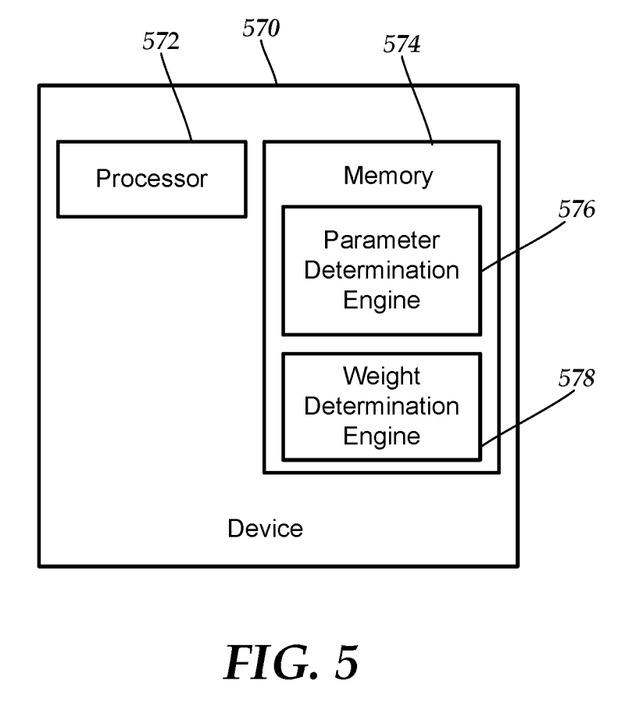
FIG. 5 is a schematic block diagram of a device with a processor and memory and a parameter adjustment engine and weight determination engine stored in the memory.

The methods described herein can be implemented in hardware or software or may combination thereof. As an example, FIG. 5 illustrates one embodiment of a device 570 that includes a processor 572 and a memory 574. The device 570 can be, for example, devices illustrated in FIG. 1, such as the IPG 14, RC 16, CP 18, or ETS 20, or any other suitable device. It will be recognized that the device 570, processor 572, and memory 574 can be replaced by multiple devices, processors, or memories, respectively and that the one or more of the processor(s) and one or more of the memory(ies) can be local or non-local.

In at least some embodiments, the memory 574 includes instructions for a parameter determination engine 576 (or a parameter determination module or parameter determination algorithm) and a weight determination engine 578 (or a weight determination module or weight determination algorithm). These engines 576, 578 are stored in the memory and operate in the processor 572 of the device 570. (In some embodiments, the engines 576, 578 can be combined into a single engine.)

Figure 6:
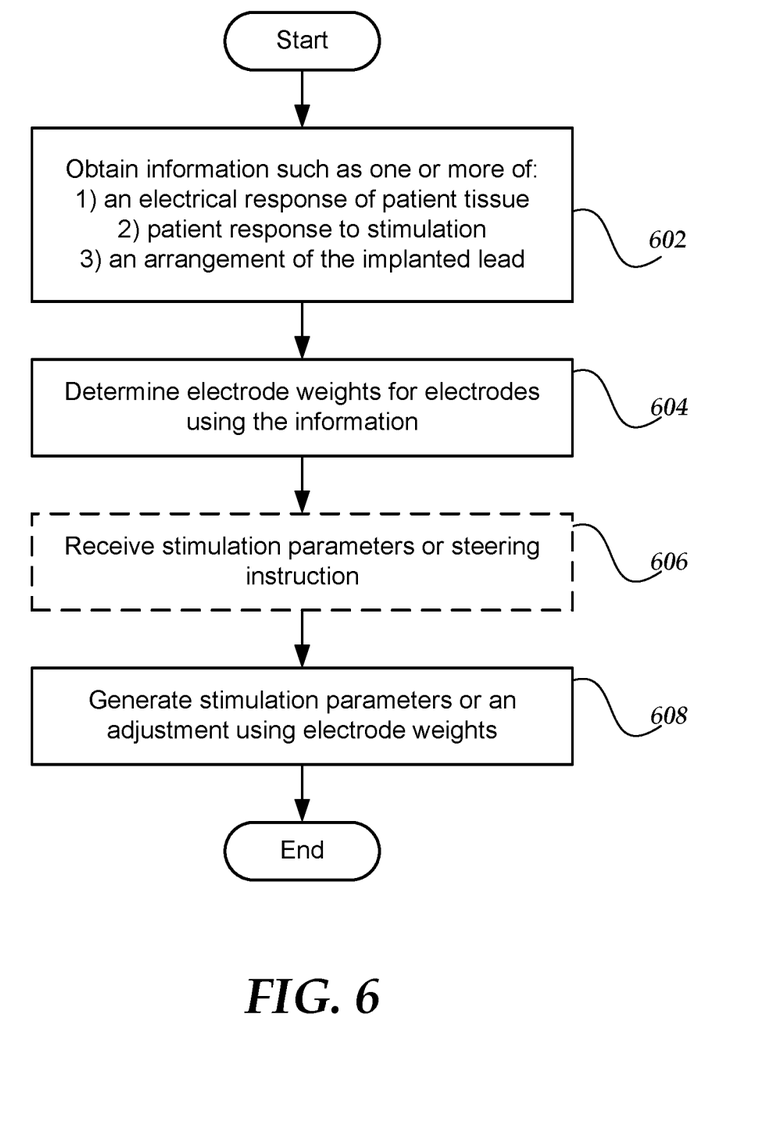
FIG. 6 is a flowchart of one embodiment of a method of determining electrode weights and determining or adjusting stimulation parameters using the electrode weights.

FIG. 6 illustrates one method of determining electrode weights and determining or adjusting stimulation parameters using the electrode weights. This method can be embodied in the parameter determination engine 576 (for example, steps 606 and 608) and weight determination engine 578 (for example, steps 602 and 604).

In step 602, information is obtained that is used to determine weights for one or more of the electrodes of a lead. The information can be any of the information described above including, but not limited to, an electrical response, such as an ESG, ECAP, evoked response, or the like, of patient tissue or features of the electrical response; patient response to stimulation (for example, patient feedback, clinician feedback, or sensor measurements/analysis or the like); or an arrangement of the implanted lead or electrodes on the lead with respect to patient anatomy, such a position of the lead or electrodes in the patient tissue (for example, a position from imaging or from the clinician that implanted the lead). In at least some embodiments, some or all of the information obtained in step 602 is patient-specific. This can lead to patient-specific electrode weights.

In step 604, electrode weights for two or more of the electrodes are determined or calculated using the information. For example, the information provided in step 602 can be used to produce a calibration, using any suitable calibration methodology, that determines a relative scale for the electrodes that is then utilized to produce the electrode weights. An example of a method of determining electrode weights is presented below with respect to FIG. 7. In at least some embodiments, the electrode weights can be in a range from 0 to 1; however, other ranges of electrode weights can also be used.

In optional step 606, one or more stimulation parameters or an instruction for steering the stimulation is received. As examples, the stimulation parameter can be a stimulation amplitude, selection of one or more electrodes for providing stimulation, selection of electrode fractionalization, or the like or any combination thereof. With respect to instructions for steering, such instructions could include moving the stimulation up or down the lead (or around the lead in the case of segmented electrodes) by changing the selection or fractionalization of the electrode(s) for providing the stimulation or increasing or decreasing the stimulation amplitude or the like or any combination thereof.

In step 608, the electrode weights are used to generate stimulation parameters, or an adjustment to current stimulation parameters. The generation of stimulation parameters may be a direction to provide a set of stimulation parameters based on a default set or based on stimulation parameters received in step 606. An adjustment to current stimulation parameters may be based on the one or more stimulation parameters or steering instruction received in step 606. As an example, the electrode weights can be used to generate, or adjust, a stimulation amplitude for each of one or more electrodes that are in the set of stimulation parameters.

In at least some embodiments, the method may include adjusting the selection of electrodes to produce a set of electrodes, and corresponding amplitudes, that can produce the same (or within a threshold of, for example, 1, 2, 5, or 10%) stimulation output. For example, stimulation may be moved from an electrode that produces a smaller effect absent a large amplitude (for example, 4-6 or 9-11 in FIG. 4) to a nearby electrode (for example, electrode 7) that can produce a larger effect at lower amplitude. In at least some embodiments, a system may automatically make such a substitution. In other embodiments, the system may present the substitution to a user for approval or confirmation.

Figure 7:
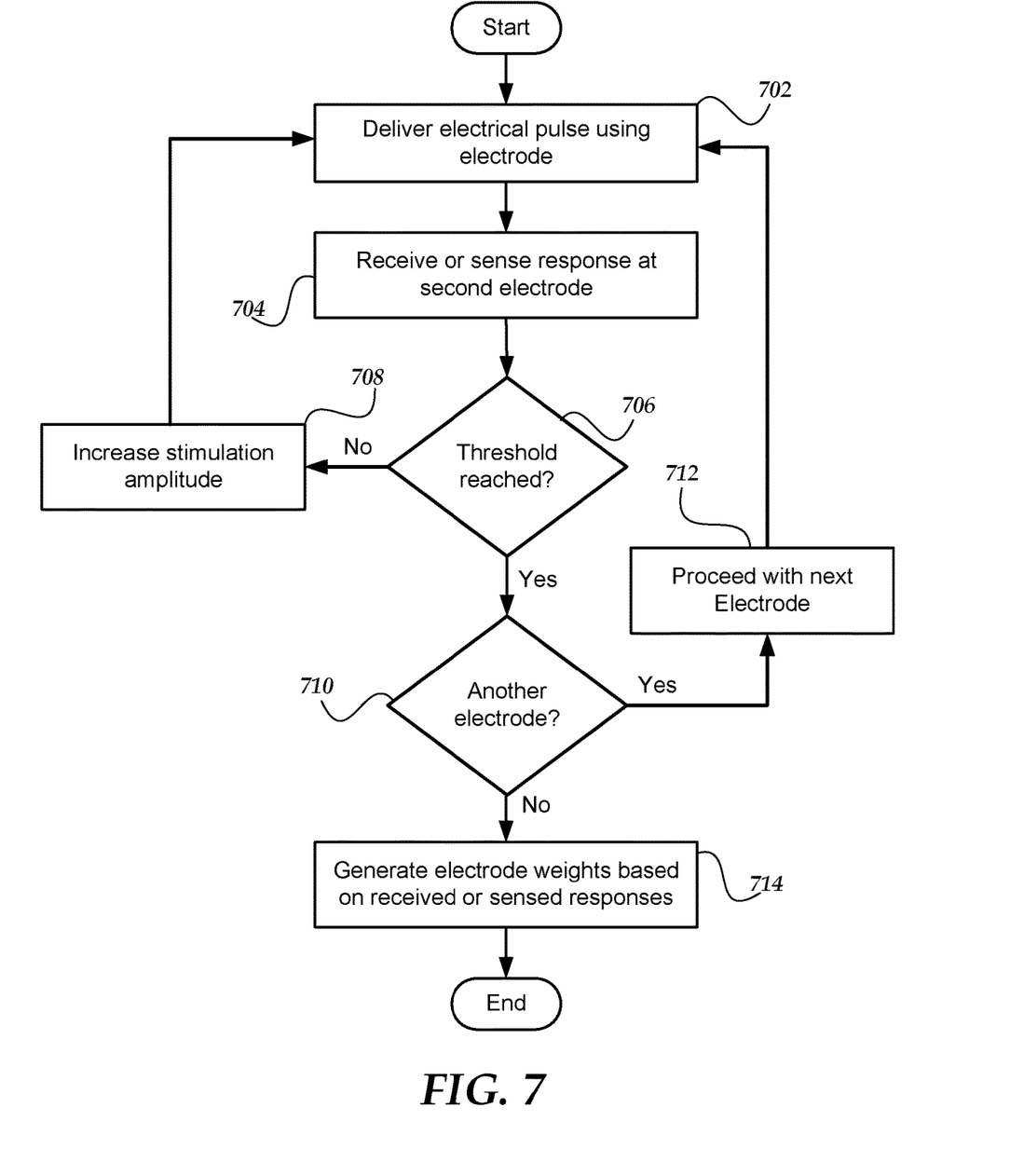
FIG. 7 is a flowchart of one embodiment of a method of determining electrode weights.

FIG. 7 illustrates one embodiment of a method for obtaining information and determining electrode weights using the information. In step 702, an electrical pulse (or multiple pulses) is delivered using one of the electrodes of a lead. Examples of such pulses and the delivery of such pulses is described above. In step 704, an electrical response is received or sensed at another electrode (or possibly even the same electrode). For example, a specific one or more of the electrodes of a lead (such as the distal-most or proximal-most electrode) can be selected for receiving or sensing the response as each of the electrodes is tested. In some other embodiments, two or more of the electrodes may be selected for receiving or sensing the response as each of the electrodes is tested.

In step 706, it is determined whether a threshold has been reached in the received or sensed response. For example, the threshold may be an amplitude threshold for the received or sensed response (for example, a perception threshold, maximum comfort threshold, intensity of the stimulation, therapeutic description or window, sensation description, or the like or any combination thereof). As another example, the threshold may be a requirement that the desired feature of the response is established or reliably measurable.

If the threshold is not reached, in step 708 the stimulation amplitude (or pulse width or the like) is increased and steps 702 to 706 are repeated until the threshold is reached or until a limit on the stimulation amplitude or other parameter is reached.

If the threshold is reached in step 706, then in step 710 it is determined whether there is another electrode to test. If yes, then steps 702 to 710 are repeated for each additional electrode.

If no (i.e., all the electrodes have been tested), then the electrode weights are generated based on the received or sensed responses in step 714. As an example, if the sensed feature is the amplitude at which a feature is established or an amplitude of the sensed feature, the highest amplitude could be normalized and then weights assigned based on the highest amplitude—for example, the amplitude for each electrode divided by the highest amplitude to give electrode weights in a range of 0 to 1.

It will be understood that each block of the flowchart illustration, and combinations of blocks in the flowchart illustration and methods disclosed herein, can be implemented by computer program instructions. These program instructions may be provided to a processor to produce a machine or engine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Figure 8:
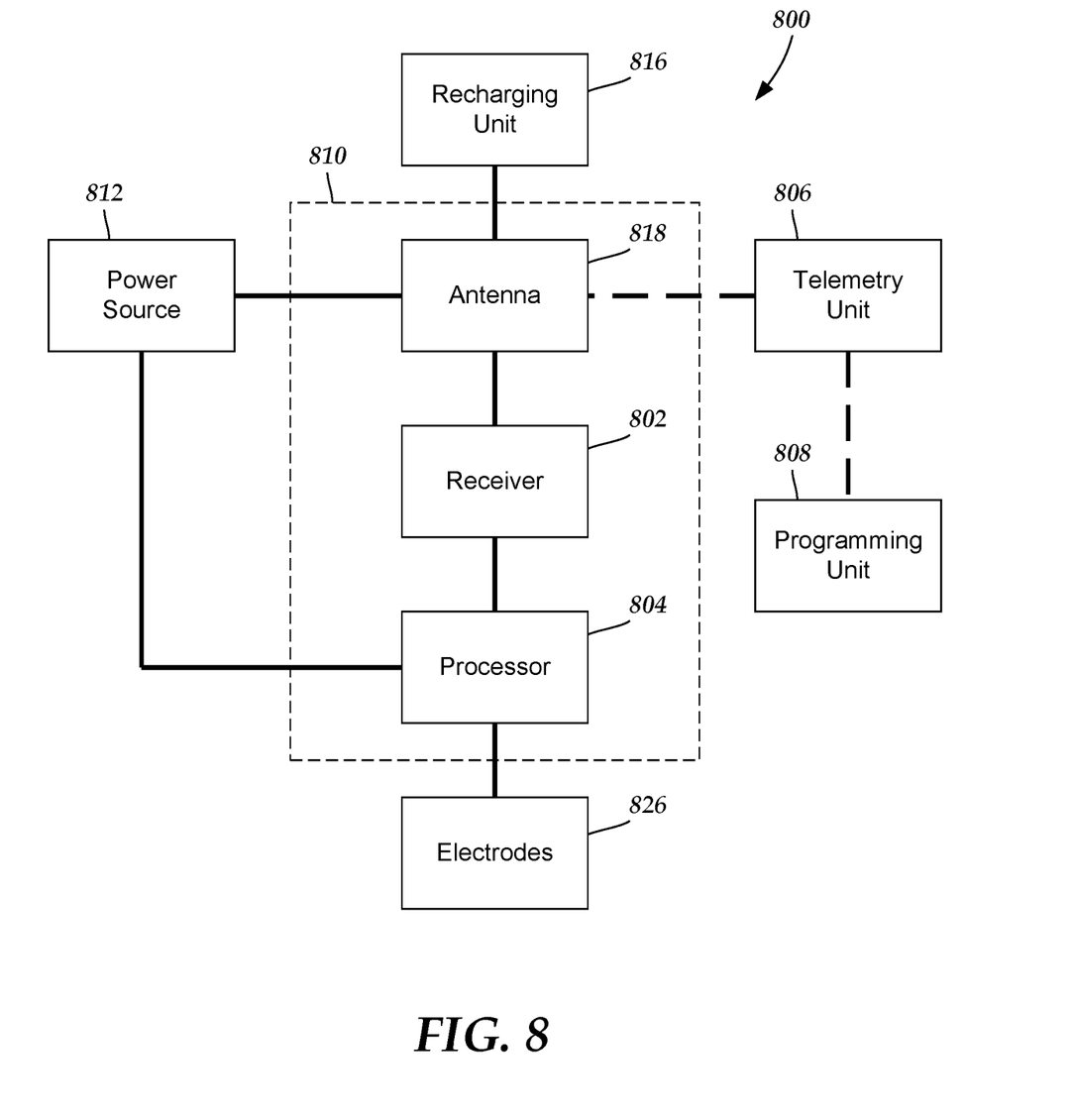
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 826 on the lead to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification provides a description of the manufacture and use of the invention. Since many embodiments of the invention can be made without departing from the spirit and scope of the invention, the invention also resides in the claims hereinafter appended.

The invention claimed is:

1. A system for generating stimulation parameters for delivery of stimulation through at least one of a plurality of electrodes of an implanted lead, comprising:
   a non-transitory memory having instructions stored thereon; and
   a processor coupled to the memory and configured to execute the instructions, the instructions comprising:
   receiving information regarding at least one of i) electrical response of patient tissue, ii) patient response to stimulation, or iii) an arrangement of the implanted lead or the electrodes of the implanted lead with respect to patient anatomy; and
   individually calculating an electrode weight for each of a plurality of the electrodes of the implanted lead based on the received information.

2. The system of claim 1, wherein the electrical response of the patient tissue comprises at least one feature of the electrical response to at least one electrical pulse delivered to patient tissue by at least one of the electrodes of the implanted lead.

3. The system of claim 1, wherein the electrical response of the patient tissue comprises an electrospinogram (ESG) or at least one feature of an ESG.

4. The system of claim 3, wherein the electrical response of patient tissue comprises at least one of an area under a curve of the ESG in a predefined time window, a range of an amplitude of the curve of the ESG in a predefined time window, a length of the curve of the ESG in a predefined time window, an energy content of the ESG in a predefined time window, a range of a derivative of the ESG in a predefined time window, a time delay of a specified signal peak of the ESG, power of the ESG in a predefined frequency band, variation of a frequency with highest energy in the ESG in a predefined frequency band, coherence changes in the ESG, a quality factor for a specified signal peak of the ESG in a predefined time window, a spectral entropy of the ESG in a predefined time window; or full width at half amplitude for a specified signal peak of the ESG in a predefined time window.

5. The system of claim 1, wherein the patient response to stimulation comprises at least one of patient feedback, clinician feedback, signals from one or more sensors, or measurements from the signals from the one or more sensors.

6. The system of claim 1, wherein the arrangement of the implanted lead or the electrodes with respect to the patient anatomy comprises a position of the implanted lead or the electrodes within the patient anatomy.

7. The system of claim 6, wherein the position is determined from imaging of the implanted lead or the electrodes within the patient anatomy.

8. The system of claim 1, wherein the arrangement of the implanted lead or electrodes with respect to the patient anatomy comprises a lateral distance of the implanted lead or electrodes from a center of the spinal cord, dorsal column, dorsal roots, or pedicles of the patient and a longitudinal position along the spinal cord of the patient.

9. The system of claim 1, wherein the instructions further comprise generating stimulation parameters, using at least one of the electrode weights, for use with the implanted lead.

10. The system of claim 9, wherein generating stimulation parameters comprises generating an adjustment, using at least one of the electrode weights, to previous stimulation parameters for use with the implanted lead.

11. The system of claim 10, wherein generating the adjustment comprises generating the adjustment in response to a steering instruction.

12. The system of claim 1, wherein the electrode weights are in a range of 0 to 1.

13. The system of claim 1, wherein receiving information comprises individually for each of a plurality of the electrodes, delivering an electrical pulse using the electrode and receiving an electrical response to the delivery, wherein the information is generated from the received electrical responses.

14. The system of claim 1, wherein the information is patient-specific information.

15. A non-transitory computer-readable medium having stored thereon instructions for execution by a processor, including:
   receiving patient-specific information regarding at least one of i) electrical response of patient tissue, ii) patient response to stimulation, or iii) an arrangement of an implanted lead or electrodes of the implanted lead with respect to patient anatomy; and
   individually calculating an electrode weight for each of a plurality of the electrodes of the implanted lead based on the received information.

16. The non-transitory computer-readable medium of claim 15, wherein the electrical response of the patient tissue comprises at least one feature of the electrical response to at least one electrical pulse delivered to patient tissue by at least one of the electrodes of the implanted lead.

17. The non-transitory computer-readable medium of claim 15, wherein the electrical response of the patient tissue comprises and electrospinogram (ESG) or at least one feature of an ESG.

18. The non-transitory computer-readable medium of claim 15, wherein the arrangement of the implanted lead or the electrodes with respect to the patient anatomy comprises a position of the implanted lead or the electrodes within the patient anatomy.

19. The non-transitory computer-readable medium of claim 15, wherein the arrangement of the implanted lead or the electrodes with respect to the patient anatomy comprises a lateral distance of the implanted lead or the electrodes from a center of the spinal cord, dorsal column, dorsal roots, or pedicles of the patient and a longitudinal position along the spinal cord of the patient.

20. The non-transitory computer-readable medium of claim 15, wherein the instructions further comprise generating stimulation parameters, using at least one of the electrode weights, for use with the implanted lead.

* * * * *